United States Patent [19]
Kageyama

[11] Patent Number: 4,787,368
[45] Date of Patent: Nov. 29, 1988

[54] MEDICAL DEVICE DRIVING SYSTEM

[75] Inventor: Toshinobu Kageyama, Toyota, Japan

[73] Assignee: Aisin Seiki Kabushiki Kaisha, Kariya, Japan

[21] Appl. No.: 882,745

[22] Filed: Jul. 7, 1986

[30] Foreign Application Priority Data

Jul. 8, 1985 [JP] Japan .................................. 60-149605

[51] Int. Cl.⁴ ............................................. A61B 19/00
[52] U.S. Cl. ........................................... 600/18; 623/3
[58] Field of Search ............. 128/1 D, 419 PG; 623/3

[56] References Cited

U.S. PATENT DOCUMENTS

| | | | |
|---|---|---|---|
| 4,016,871 | 4/1977 | Schiff ................................... | 128/1 D |
| 4,175,264 | 11/1979 | Schiff ................................... | 128/1 D |
| 4,485,818 | 12/1984 | Leckrone et al. ............. | 128/419 PG |
| 4,583,525 | 4/1986 | Suzuki et al. ......................... | 128/1 D |
| 4,597,381 | 7/1986 | Oumi et al. ........................... | 128/1 D |
| 4,648,385 | 3/1987 | Oumi et al. ........................... | 128/1 D |

*Primary Examiner*—Max Hindenburg
*Attorney, Agent, or Firm*—Sughrue, Mion, Zinn, Macpeak & Seas

[57] ABSTRACT

A system for driving a medical device includes a positive pressure source; a first electromagnetic valve connected with the positive pressure source; an negative pressure source; a second electromagnetic valve connected with the negative pressure source; and an electronic control for switching the first and second electromagnetic valves at a predetermined timing. The electronic control includes a setting circuit for setting the switching timing of the first and second electromagnetic valves to generate a setting timing signal; a switching arrangement for switching the first and second electromagnetic valves in response to the setting timing signal of the setting circuit; a memory having a plurality of operation modes for inhibiting the operation of the switching circuit at a predetermined ratio to a predetermined number of the setting timing signal; and switches for selecting one of the operation modes of the memory means.

2 Claims, 7 Drawing Sheets

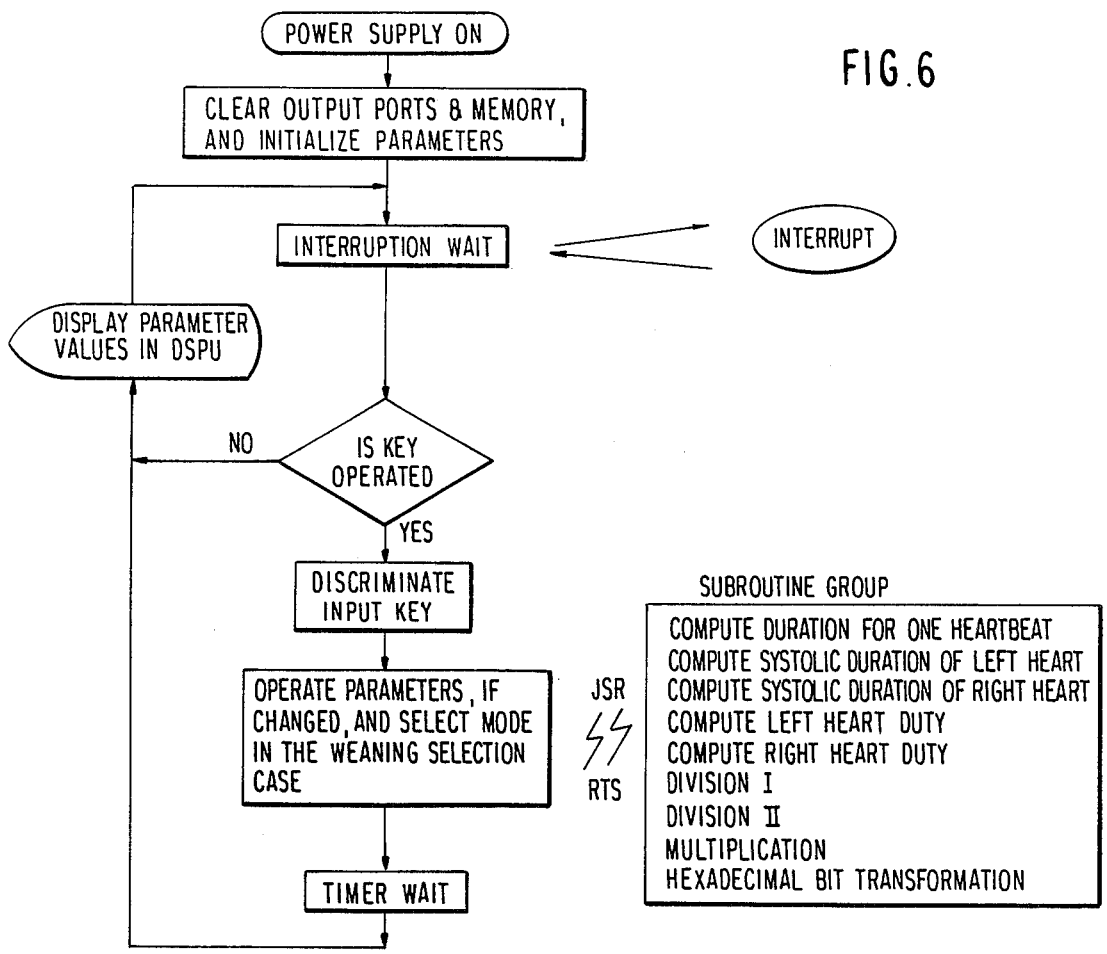

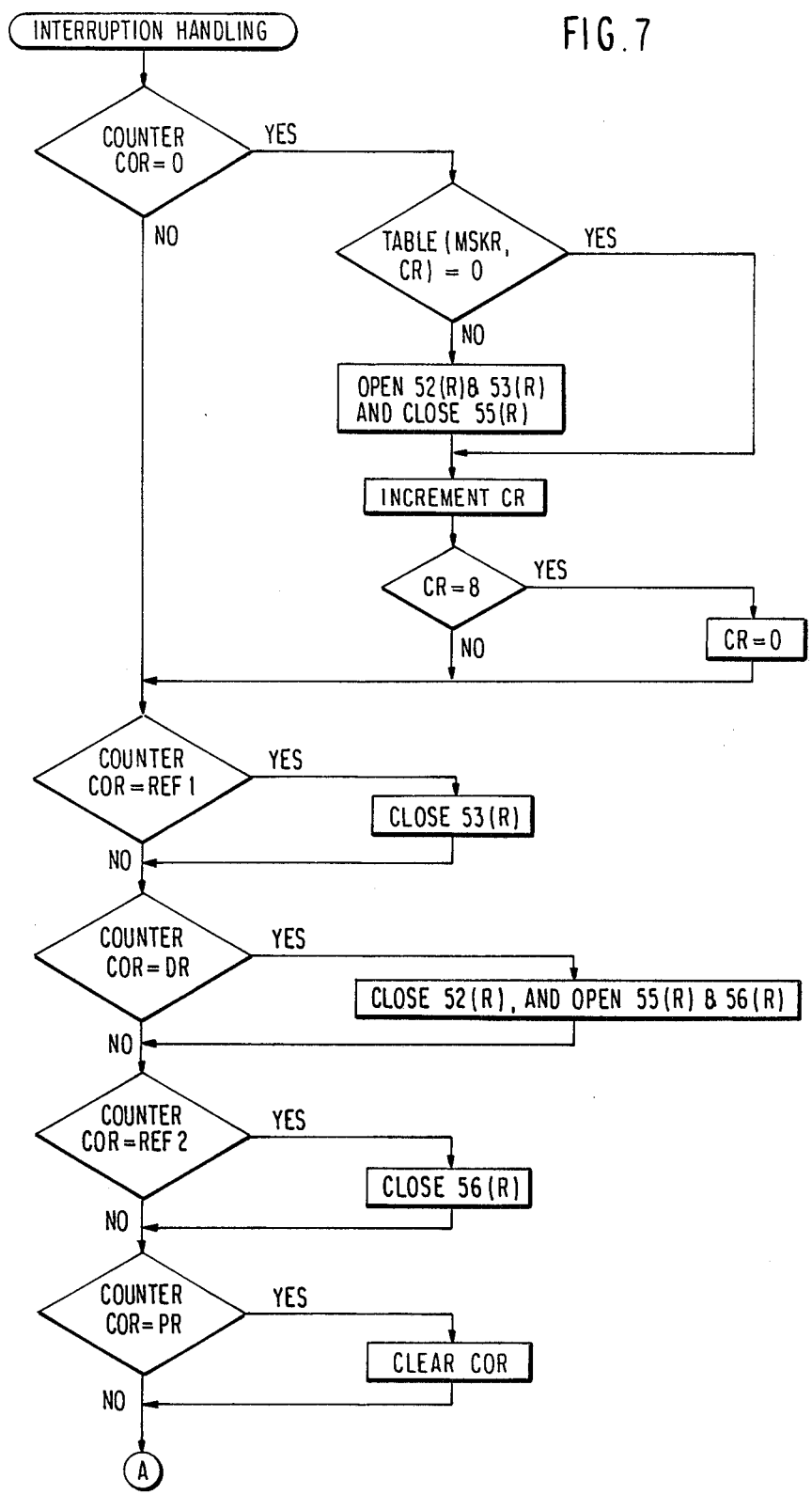

MEDICAL DEVICE DRIVING SYSTEM

BACKGROUND OF THE INVENTION

The present invention relates to a system for driving a medical device adapted to be used for auxiliary circulation, such as an assisting artificial heart or an intra-aortic balloon pump and, more particularly, to a driving system having a variable assistance ratio. Generally speaking a medical device for auxiliary circulation such as an assisting artificial heart or an intra-aortic balloon pump is used in a patient whose heart is functioning so badly that it cannot maintain necessary blood circulation. A driving system for such a medical device is usually triggered by the cardiogram of the patient. When the heart is restored to its intrinsic function, the medical device is removed from the patient's body. If, however, this removal is made suddenly, it could have an adverse influence upon the body. Therefore, the method of removal of the medical device from the body involves gradually reducing the assistance ratio. This method is usually called "weaning". The driving system of the prior art is exemplified by U.S. Pat. No. 4,016,871 and U.S. Pat. No. 4,175,264. The system, as disclosed, employs the R-waves of the cardiogram. When a trigger signal is inputted, a solenoid pulse signal for supplying positive and negative pressures to the medical device in synchronism with a predetermined timing is outputted to effect diastole and systole of the medical device.

In this system, the limit for the pulse signal is arranged with a frequency divider for carrying out the weaning. By selecting 1/2 or 1/4 as the assistance ratio by means of a push button, the pulse signal is gradually dropped to effect the weaning.

In the driving system disclosed above, however, the assistance ratio has its allowable selection limited to one of 1/1, 1/2, and 1/4, and its change is not divided equally. This makes it difficult to finely cope with the particular state of the patient. Since the disclosed device changes the assistance ratio by dividing the frequency of the pulse signal, it cannot set an assistance ratio between 1/1 and 1/2.

SUMMARY OF THE INVENTION

It is, therefore, an object of the present invention to provide a medical device driving system which is enabled to perform the weaning function more precisely by dividing the assistance ratio equally. According to the present invention, there is provided a system for driving a medical device comprising: a positive pressure source; a first electromagnetic valve connected with said positive pressure source; a negative pressure source; a second electromagnetic valve connected with said negative pressure source; and electronic control means for switching said first and second electromagnetic valves at a predetermined timing wherein the improvement resides in that said electronic control means includes: setting means for setting the switching timing of said first and second electromagnetic valves to generate a setting timing signal; switching means for switching said first and second electromagnetic valves in response to the setting timing signal of said setting means; memory means having stored therein a plurality of operation modes for inhibiting the operation of said switching means at a predetermined ratio to a predetermined number of said setting timing signal; and switch means for selecting one of the operation modes of said memory means.

According to the driving system of the present invention when the first and second electromagnetic valves are to be switched at the timing set by the setting means, this timing can be inhibited even if it arrives in accordance with the operation mode selected by the switch means. This makes it possible to select the weaning ratio by the operation of the switch means. At this time, an arbitrary ratio can be set by storing in advance the operation mode to be selected in the memory means. As a result, the weaning can be conducted precisely in conformity with the state of the patient by storing the fine ratios to be set.

The foregoing and other objects, features and advantages of the invention will be apparent from the following more particular description of a preferred embodiment of the invention with reference to the accompanying drawings.

BRIEF DESCRIPTION OF THE DRAWINGS

FIGS. 6, 7, and 8 are flow charges showing the schematic operations of the electronic control unit ECU2 shown in FIG. 5.

FIG. 5 is a diagram showing a memory table stored in the electronic control unit ECU of FIG. 5.

DETAILED DESCRIPTION OF THE PREFERRED EMBODIMENT

The embodiment of the present invention will be described as follows with reference to the accompanying drawings.

Figure 1:
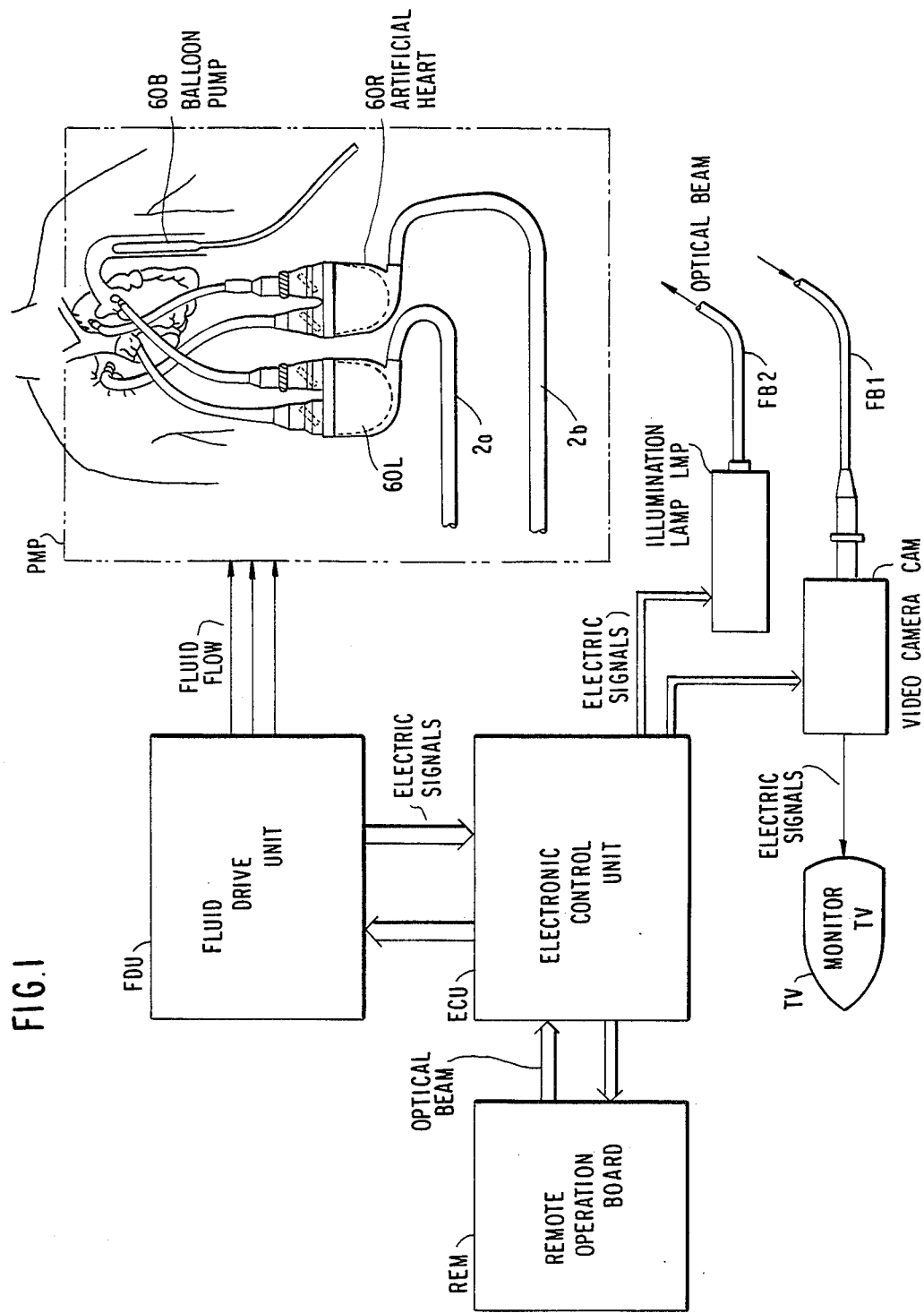
FIG. 1 is a block diagram showing the construction of a system for driving an artificial heart and a balloon pump in accordance with one embodiment of the present invention.

FIG. 1 shows the construction of the medical device driving system for driving artificial hearts and an intra-aortic balloon pump. In FIG. 1, reference numerals 60L and 60R denote artificial hearts, and numeral 60B denotes the balloon pump to be inserted into a main artery. A fluid drive unit FDU is equipped with three fluid drive output terminals. As a matter of fact, however, no state is considered in which the artificial hearts 60L and 60R and the balloon pump 60B are simultaneously used. The driving system is so constructed that only two of them can operate together. An electronic control unit ECU for controlling the fluid drive unit FDU is connected with a remote operation board REM.

Figure 2:
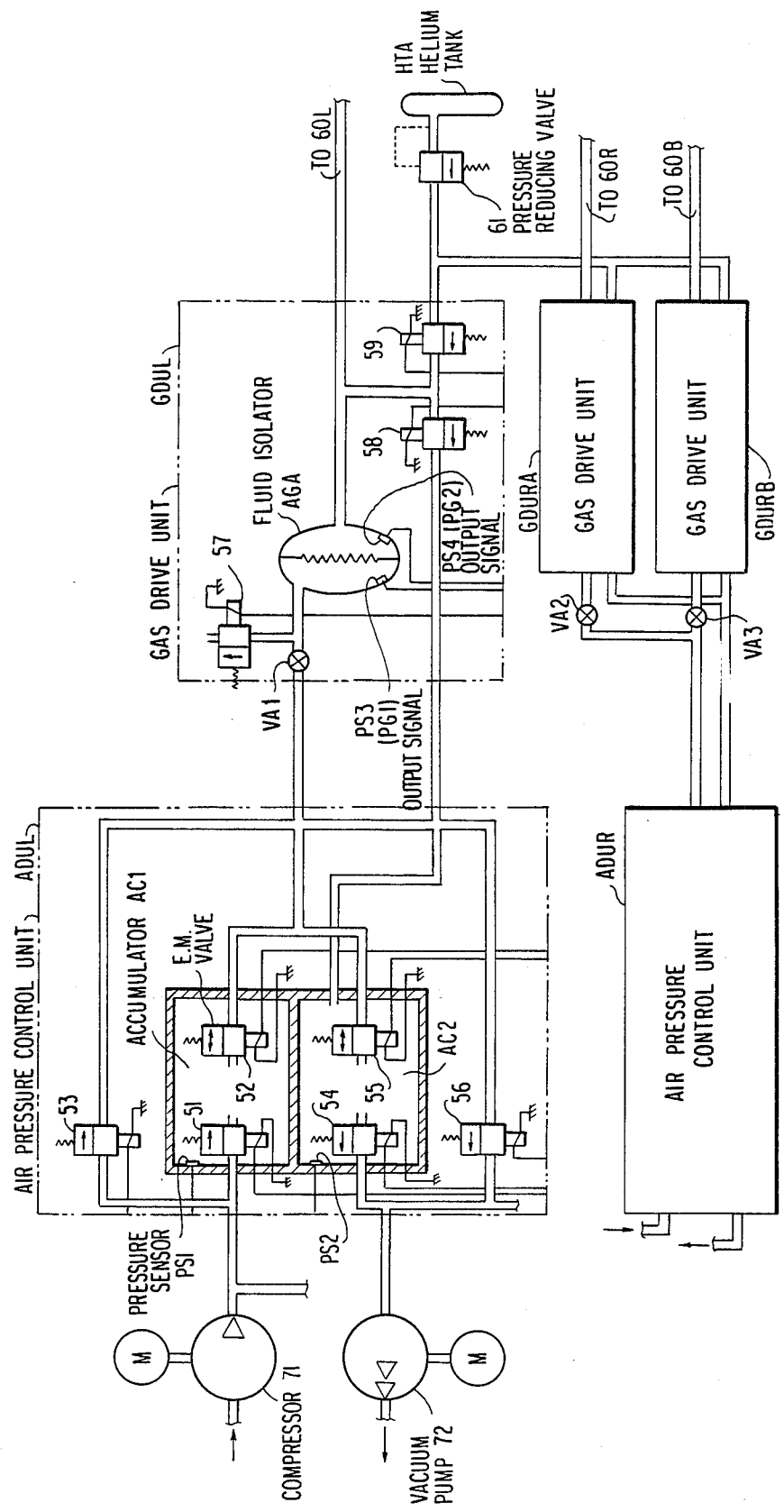
FIG. 2 is a block diagram showing the construction of a fluid drive unit FDU shown in FIG. 1.

FIG. 2 shows the construction of the fluid drive unit FDU, which will be schematically explained at first. The fluid drive unit FDU is constructed of a compressor 71, a vacuum pump 72, air pressure control units ADUL and ADUR, gas drive units GDUL, GDURA and GDURB, a helium gas tank HTA and a pressure reducing valve 61. The gas drive unit GDUL has its input end connected with the output end of the air pressure control unit ADUL, and the gas drive units GDURA and GDURB have their input ends connected commonly with the output end of the air pressure control unit ADUR. The gas drive units GDUL, GDURA and GDURB in turn have their output ends connected with the artificial hearts 60L and 60R and the balloon pump 60B, respectively.

The air pressure control unit ADUL will be specifically described in the following. This unit is equipped with six electromagnetic valves 51, 52, 53, 54, 55, and 56. Of these, the electromagnetic valves 51, 51, and 53, are used for establishing positive pressures whereas the electromagnetic valves 54, 55, and 56, are used for establishing negative pressures. The electromagnetic valves 51 and 52 are disposed in an accumulator AC1 whereas the electromagnetic valves 54 and 55 are disposed in an accumulator AC2. The electromagnetic valves 51 and 53 have their input ends connected with the output end of the compressor 71; the electromagnetic valves 54 and 56 have their input ends (which are located downstream with respect to the fluid flow direction) connected with the negative pressure output end of the vacuum pump 72, and the electromagnetic valves 52, 53, 55, and 56, have their output ends connected with the output end of the air pressure control unit ADUL. Pressure sensor PS1 and PS2 are for for detecting the respective pressures prevailing in the accumulators AC1 and AC2. The air pressure control unit ADUR has the same construction as that of the unit ADUL described above.

Next the gas drive unit GDUL will be described. This unit is equipped with electromagnetic valves 57, 58, and 59, and a fluid isolator AGA. This fluid isolator AGA has its primary (i.e., air) side connected through a mechanical valve VA1 with the output end of the aforementioned air pressure control unit ADUL. The electromagnetic valve 57 has its input end connected with the primary side of the fluid isolator AGA and its output end vented to the atmosphere. The electromagnetic valve 59 has its input end connected with the output end of the pressure reducing valve 61 and its output end connected with the secondary side of the fluid isolator AGA. The electromagnetic valve 58 has its input end connected with the secondary side of the fluid isolator AGA and its output end connected with the inside of the aforementioned accumulator AC2. The fluid isolator AGA is equipped with pressure sensors PS3 and PS4, respectively, at its primary and secondary sides. The gas drive units GDURA and GDURB have the same construction as that of the unit GDUL described above.

Figure 3:
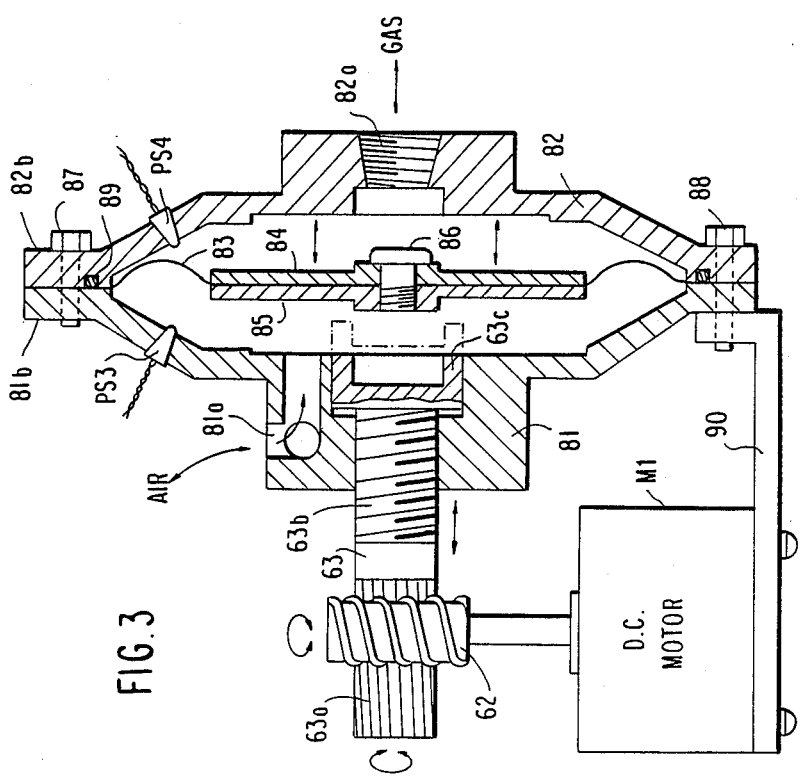
FIG. 3 is a longitudinal section showing the construction of a fluid isolator AGA incorporated into a gas drive mechanism GDURB.

FIG. 3 shows the construction of the fluid isolator AGA which is incorporated into the gas drive unit GDURB. For brevity, the fluid isolator AGA is constructed such that a diaphragm 83, sandwiched at its periphery between housings 81 and 82, partitions the inside into a compartment communicating with a primary port 81a and a compartment communicating with a secondary port 82a. The diaphragm can be moved to the right and left as viewed in FIG. 3.

The diaphragm 83 has its central portion sandwiched between plates 84 and 85. A bolt 86 fastens the plates 84 and 85 together. On the central portion of the housing 81, there is mounted a regulating member 63 for adjusting the displacement of the plate 85. This regulating member 63 is threaded as shown at 63a and 63b and engaged with the housing 81 by means of the thread 63b.

If the regulating member 63 is turned, it is moved to the right and left. The moving range of the plates 84 and 85 is enlarged for the leftward movement but is restricted for the rightward movement. A DC motor has a drive shaft with a worm gear 62 fixed thereon which in turn is in meshing engagement with the tread 63a. As a result, the drive of the motor M1 will change the moving range of the plates 84 and 85. The motor M1 is made stationary through a base plate 90 with respect to a flanged portion 81b of the housing 81. The housings 81 and 82 are secured together with an O-ring 89 therebetween by means of bolts 87 and 88.

The fluid isolators AGA incorporated into the gas drive units GDUL and GDURa are made to have the same construction as that of the isolator AGA of FIG. 3 except that the motor M1 is omitted therefrom.

Figure 4:
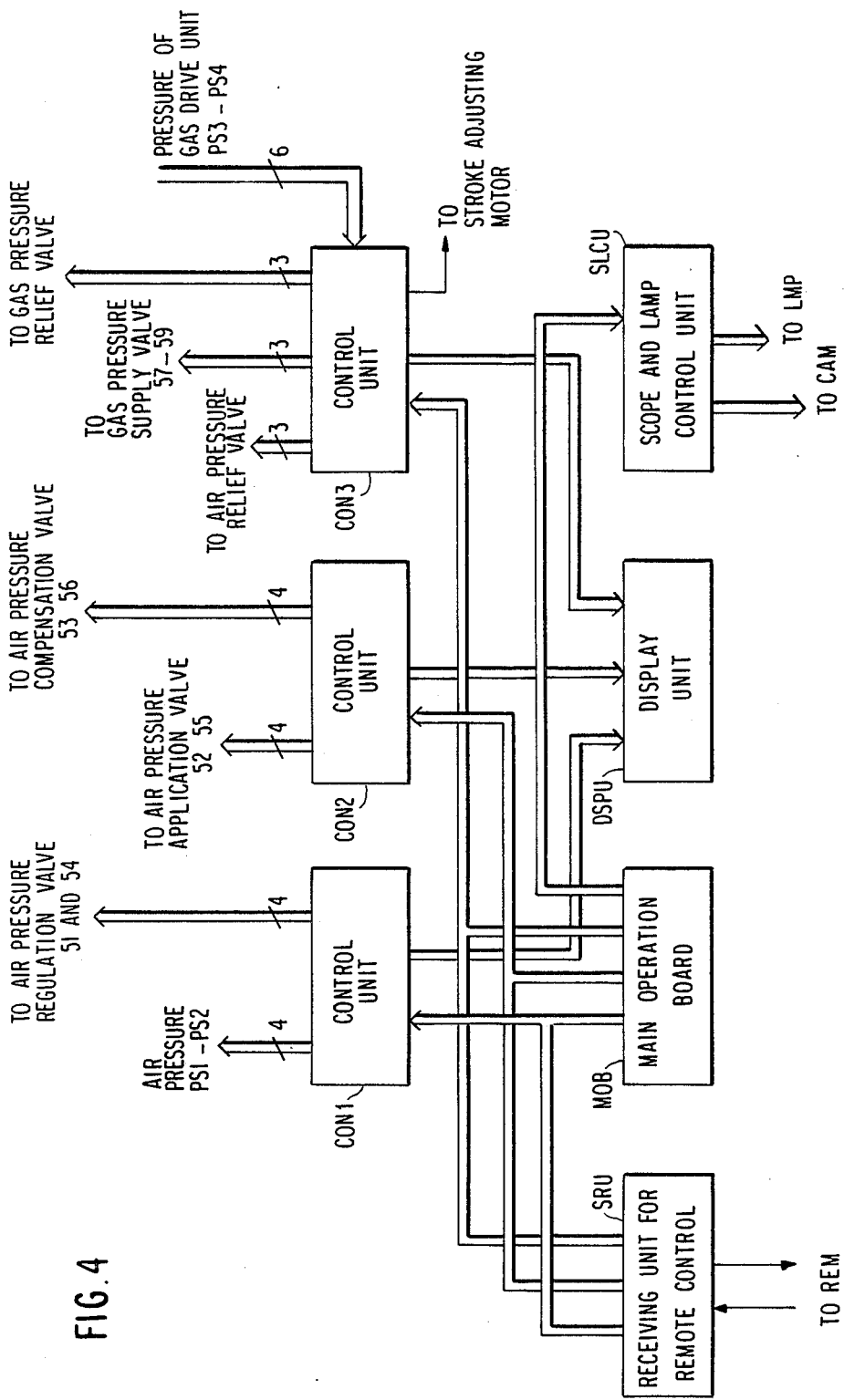
FIG. 4 is a block diagram showing the construction of an electronic control unit ECU shown in FIG. 1.

FIG. 4 shows the construction of the electronic control unit ECU shown in FIG. 1. With reference to FIG. 4, this electronic control unit ECU is constructed of control units CON1, CON2, and CON3, a receiving unit SRU for remote control, a main operation board MOB and a display unit DSPU.

The control unit CON1 monitors the output signals of the pressure sensors PS1 and PS2 of the air pressure control units ADUL and ADUR to open and close the electromagnetic valves 51 and 54 so that the pressures in the accumulators AC1 and AC2 may become equal to set levels.

The control unit CON2 opens and closes the electromagnetic valves 52, 53, 55, and 56, of the air pressure control units ADUL and ADUR at predetermined timings according to set heartbeat and right and left systolic durations or duties.

The control unit CON3 controls of the electromagnetic valves 57, 58, and 59, of the gas drive units GDUL, GDURA and GDURB, but not the latter two units GDURA and GDURB simultaneously. These controls of the gas drive units GDUL, GDURA, and GDURB, are performed by monitoring either the output signals (PG1 and PG2) of the pressure sensors PS3 and PS4 or the output signal of the latter sensors PS4 only. For the control of the gas drive mechanism GDURB, moreover, the motor M1 is controlled.

The display unit DSPU is composed of a multiplicity of 7-segment displays and is connected with the control units CON1, CON2 and CON3. The main operation board MOB is also connected with the control units CON1, CON2, and CON3. The remote control receiving unit SRU has its respective output lines connected like the corresponding signal lines of the main operation board MOB.

Figure 5:
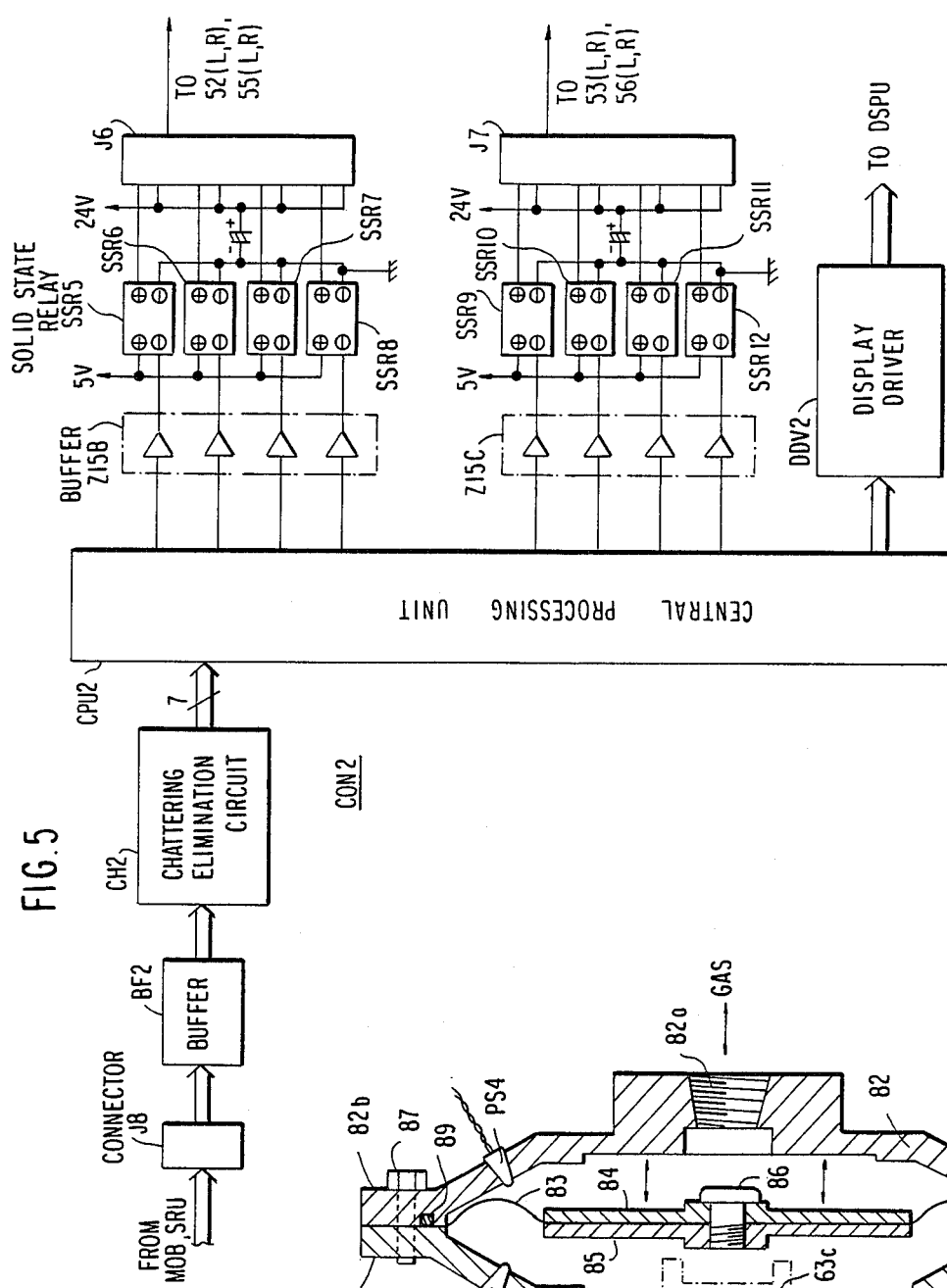
FIG. 5 is a block diagram showing the construction of a control unit CON2 shown in FIG. 4.

FIG. 5 shows the construction of the control unit CON2 of FIG. 4. The description will proceed with reference to FIG. 5. This control unit CON2 is primarily composed of a central processing unit CPU2. A connector J8 connected with the main operation board MOB and the remote control receiving unit SRU is connected with the input port of the central processing unit CPU2 through a buffer BF2 and a chattering elimination circuit CH2.

The connector J8 is fed with a plurality of signals such as the UP and DOWN signals of the heartbeat, the UP and DOWN signals of an R-side duty, the UP and DOWN signals of an L-side duty or a later described signal for selecting the set weaning value. The central processing unit CPU2 has its eight output ports connected through buffers Z15B and Z15C with solid state relays SSR5 to SSR12. Of these, the solid state relays SSR5 to SSR8 are connected with the air pressure applying electromagnetic valves 52 (L and R) and 55 (L and R), respectively, and the solid state relays SSR9 to SSR12 are connected with the air pressure compensating electromagnetic valves 53 (L and R) and 56 (L and R), respectively. The central processing unit CPU2 has its display signal output port connected with a display driver DDV2, which in turn has its output terminal connected with the display unit DSPU.

Figure 8:
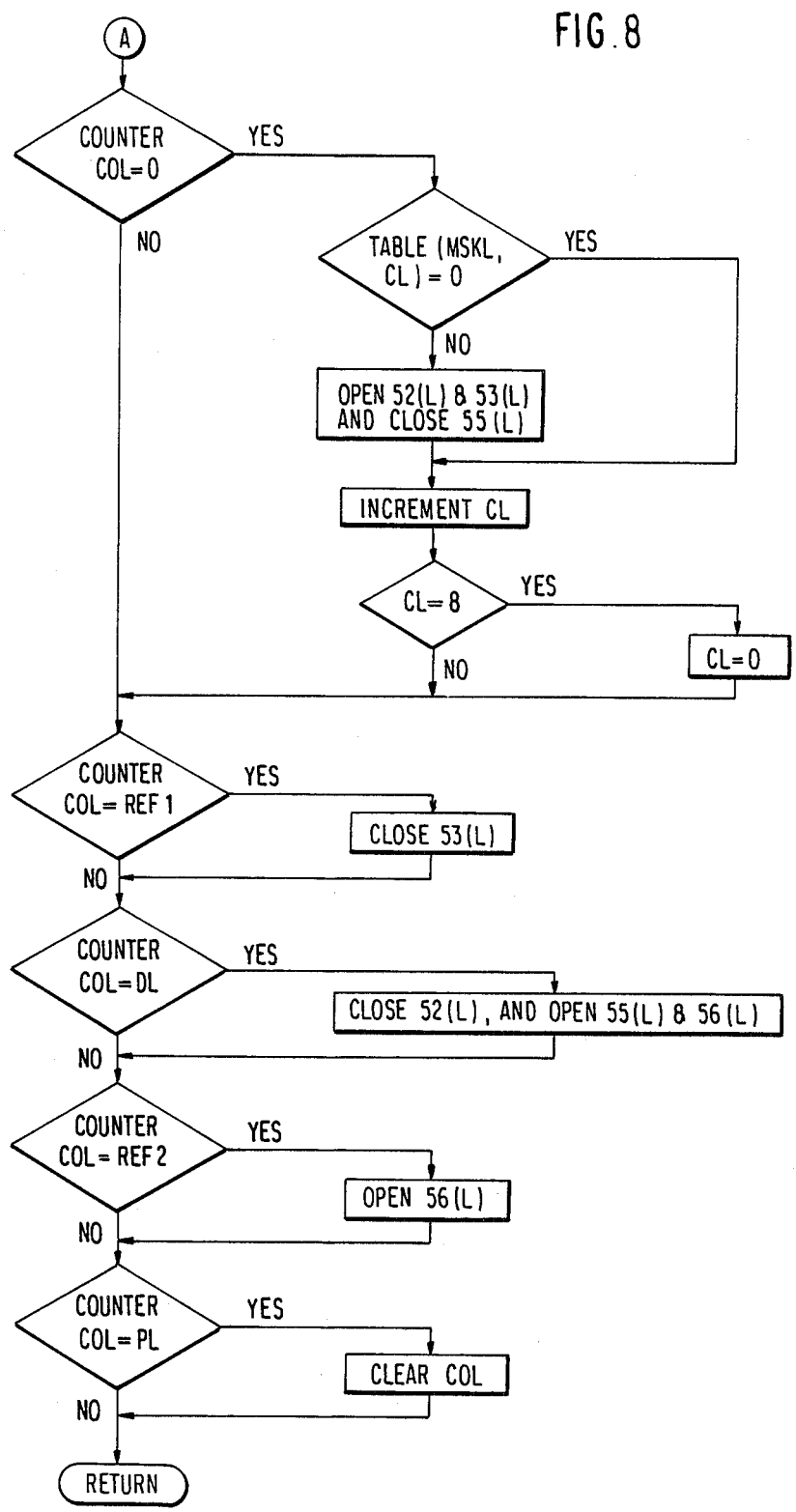

The operations of the central processing unit CPU2 are schematically shown in FIGS. 6, 7, and 8. Of these, FIG. 6 shows a main routine, and FIGS. 7 and 8 show interruption handling routines. The description will proceed with reference to FIGS. 6, 7, and 8.

When the power is supplied, the central processing unit CPU2 sets its output ports at initial levels, clears the contents of a random access memory (i.e., RAM), reads out values stored in advance in a read only memory (i.e., ROM), and sets parameters at initial values.

These parameters of the central processing unit CPU2 are exemplified by the heartbeat number PR, the duty DL of the left artificial heart and the duty DR of the right artificial heart. In this example, more specifically, the heart beat number PR is set at an initial value of 100 r.p.m., the duty DL is set at an initial value of forty-five percent (i.e., a systolic duration of 270 ms), and the duty DR is set at an initial value of fifty-five percent (i.e., a systolic duration 330 ms).

Next the processing loop including an interruption wait, a check of key inputs from the operation board and a parameter display is executed. A key input, if any, has its kind discriminated and its value compared with the upper and lower limits of desired value of the parameters to be changed, and the changed parameters and their relating parameters are arithmetically processed. These processings are conducted while a variety of subroutines are being executed. With a key input instructing the selection of a set weaning value, a predetermined portion of the matrix of a later described memory table TABLE is selected on the basis of that key operation.

Next the interruption handling will be described as follows. The values of counters COR and COL are counted up by one for each interruption handling. When the counted values take the value PR (i.e., a time parameter determined by the heartbeat number), they are cleared to zero. When the counter COR takes the value 0, reference is made to the memory table TABLE stored with the operation modes. This memory table TABLE is shown in FIG. 9. Since the medical device driving system of the present invention uses the 8-bit microprocessor, as has been described hereinbefore, the matrix is so constructed as is shown in FIG. 9. The storing operation mode of the memory means is conditioned to satisfy the following formula thereby to set an operation inhibiting ratio:

$$\frac{(n - a)}{n} : 0 \leq a \leq n - 1$$

wherein letter a designates an integer. Specifically, the memory table TABLE is stored with the eight weaning modes. Moreover, these modes 1 to 8 are set at assistance ratios of 1/1 (i.e., 8/8), 7/8, 3/4 (i.e., 6/8), 5/8, 1/2 (i.e., 4/8), 3/8, 1/4 (i.e., 2/8) and 1/8, respectively. This matrix has its modes selected by the key operation, and the mode thus selected is designated by the table TABLE (MODE, CR) in the flow chart of FIG. 7. Incidentally, FIG. 9 shows only the matrix relating to the counter COR, whereas the matrix of the counter COL is omitted because it may have identical stored modes although it is different from the former in that the memory table is designated by another table TABLE (MODE, CL). The interruption handling will be described with reference to the matrix of FIG. 9. For simplicity, incidentally, the description to be made here is directed to the case in which the mode 3 is selected.

When the counter COR takes the value 0, reference should be made to the column CR=0 and the MODE 3 in the memory table TABLE. Since this column is designated at "1", the individual valves are driven, that is, the valves are 52(R) and 53(R) are opened whereas the valve 55(R) is closed (to apply the positive pressure). In order to make the next reference to the next column, the value CR is incremented. As a result, the incrementation is conducted until the value CR reaches 8, whereupon the value CR is cleared to 0, because the memory table is composed of the eight bits, as has been described above. When the value of the counter COR takes a reference value REF1 (i.e., the value for regulating the time period for which the positive pressure compensating electromagnetic valve 53 is open), this valve 53(R) is closed. When the value of the counter COR take the value DR of the duty parameter, the valves 55(R) and 56(R) are opened, whereas the valve 52(R) is closed (to apply the negative pressure). On the other hand, when the value of the counter COR takes another reference REF2 (i.e., the value for regulating the time period) for which the negative pressure compensating electromagnetic valve 56 is open), this valve 56 is closed. After these processings, the counter COR is counted up.

Likewise, when the counter COL takes the value 0, reference should be made of a column of CL=0 of the mode 3 in the memory table TABLE. Since this column is designated at "1", the individual valves are driven, that is, the valves 52(L) and 53(L) are opened whereas the valve 55(L) is closed (to apply the positive pressure). In order to make the next reference to the next column, the value CL is incremented. As a result, the incrementation is conducted until the value CL reaches 8, whereupon the value CL is cleared to 0, because the memory table is composed of the eight bits, as has been described above.

When the value of the counter COL takes the reference value REF1 (i.e., the value for regulating the timer period for which the positive pressure compensating electromagnetic valve 53 is open), this valve 53(L) is closed. When the value of the counter COL takes the value D1 of the duty parameter, the valves 55(L) and 56(L) are opened, whereas the valve 52(L) is closed (to apply the negative pressure). On the other hand, when the value of the counter COL takes the reference value REF2 (i.e., the value for regulating the time period for which the negative pressure compensating electromagnetic valve 56 is one), this valve 56 is closed. After these processings, the counter COL is counted up.

In short, the electromagnetic valves 52, 53, 55, and 56 are actuated. In these actuations, the valve 56 is controlled to be temporarily opened after the switching operation from the negative to positive pressures so that the pressure steeply rises and breaks to have a square pressure wave. Here, the electromagnetic valve 56 may be omitted because the (breaking) rate in case the pressure is turned from positive to negative values exerts no serious influences upon the drive of the artificial hearts.

By the controls thus far described, one interruption handling is effected at the predetermined timing. The next two interruption handlings are conducted in the same manner for MODE 3. When the counter COR takes the value 3, reference is made to the column of CR=3 in the memory table TABLE. Since this column is designated at "0" for MODE3, the individual valves 52(R), 53(R) and 55(R) are not controlled. Therefore, only the value CR is incremented. The subsequent processings are unvaried because the valves 52(R), 53(R) and 55(R) are not set.

Likewise when the counter COL takes the value 3, the valves 52(L), 53(L) and 55(L) are not set because the column of CL=3 in the MODE3 of the memory table TABLE is designated at "0". As a result, even when the predetermined timing is reached, the electromagnetic valves are not set to inhibit applications of the positive and negative pressures.

After these operations, the controls designated by the matrix are conducted for each interruption handling with reference to the memory table TABLE.

It is not necessary to describe the remaining constructions and operations of the remote operation board REM shown in FIG. 1 and the control units CON1 and CON3, the remote control receiving unit SRU, the main operation board MOB, and the display unit DSPU shown in FIG. 4, because the constructions and operations may be identical to those of Japanese patent application No. 58-213748, belonging to the common assignee.

According to the present invention, the weaning can be effected by inhibiting the set timing, even if the latter arrives, in accordance with the operation mode selected by the switch means. Moreover, the weaning can be made precise in accordance with the state of the patient because its ratio is stored in advance in the memory means so that it can be set at an arbitrary value.

While the invention has been particularly shown and described with reference to preferred embodiments thereof it will be understood by those in the art that the foregoing and other changes in form and details may be made therein without departing from the spirit and scope of the invention.

What is claimed is:

1. A system for driving a medical device, comprising:
    a positive pressure source;
    a first electromagnetic valve connected with said positive pressure source;
    a negative pressure source;
    a second electromagnetic valve connected with said negative pressure source; and
    electronic control means for controlling said first and second electromagnetic valves,
    said electronic control means comprising setting means for setting a switching timing of said first and second electromagnetic valves; switching means for switching said first and second electromagnetic valves according to said switching timing; memory means for storing a plurality of assistance ratios; and selecting switch means, said electronic control means selecting one of said assistance ratios according to a condition of said selecting switch means and inhibiting an operation of said switching means according to said selected assistance ratio.

2. A medical device driving system according to claim 1, wherein said electronic control means is constructed of an n-bit microprocessor, and wherein the storing operation mode of said memory means is conditioned to satisfy the following formula thereby to set an operation inhibiting ratio:

$$\frac{(n-a)}{n} : 0 \leq a \leq n-1$$

wherein letter a designates an integer.

* * * * *